United States Patent [19]
Ku et al.

[11] Patent Number: 5,668,143
[45] Date of Patent: Sep. 16, 1997

[54] HETEROCYCLIC BENZENESULFONYLIMINE DERIVATIVES AS INHIBITORS OF IL-1 ACTION

[75] Inventors: George Ku, Burlington, Mass.; Boyd L. Harrison, Cincinnati; David M. Stemerick, Fairfield, both of Ohio

[73] Assignee: Merrell Pharmaceuticals Inc., Cincinnati, Ohio

[21] Appl. No.: 648,150

[22] PCT Filed: Nov. 3, 1994

[86] PCT No.: PCT/US94/12575

§ 371 Date: Jul. 3, 1996

§ 102(e) Date: Jul. 3, 1996

[87] PCT Pub. No.: WO95/14670

PCT Pub. Date: Jun. 1, 1995

Related U.S. Application Data

[63] Continuation of Ser. No. 158,661, Nov. 29, 1993, abandoned.

[51] Int. Cl.$^6$ .......... A61K 31/44; A61K 31/38; A61K 31/35; A61K 31/16
[52] U.S. Cl. .......... 514/299; 514/312; 514/313; 514/432; 514/457; 514/539; 514/608; 514/620
[58] Field of Search .......... 514/457, 313, 514/312, 299, 432, 539, 608, 620

[56] References Cited

U.S. PATENT DOCUMENTS

| | | | |
|---|---|---|---|
| 3,742,951 | 7/1973 | Zadffaroni | 128/268 |
| 3,797,494 | 3/1974 | Zadffaroni | 128/268 |
| 3,921,636 | 11/1975 | Zaddaroni | 128/260 |
| 3,996,934 | 12/1976 | Zadffaroni | 128/268 |
| 4,031,894 | 6/1977 | Urquhart et al. | 128/268 |

FOREIGN PATENT DOCUMENTS

| | | |
|---|---|---|
| 0303387 | 2/1988 | European Pat. Off. . |
| 9215565 | 9/1992 | WIPO . |

OTHER PUBLICATIONS

Richard L. Jackson et al, *Current Drugs: Anti–Atherosclerotic Agents*, Oct. 1991, pp. B31–B41.

Ivan G. Otterness et al, *Cytokine*, vol. 3, No. 4 (Jul.) 1991: pp. 277–283.

Kjell Ohlsson et al, *Nature*, vol. 348, Dec. 6 1990, pp. 550–552.

Masayuki Matsuda et al, *Journal of Neurological Sciences*, 102 (1991) pp. 100–104.

Pierre F. Piguet et al, *Cytokine*, vol. 5, No. 1 (Jan.) 1993: pp. 57–61.

Stellan Sandler et al, *Autoimmunity*, 1991, vol. 10: pp. 241–253.

Nobuyuki Miyasaka et al, *Arthritis and Rheumatism*, vol. 31, No. 4 (Apr. 1988).

Scott K. Durum et al,*Ann. Rec. Immunol*, 1985: pp. 263–287.

R.Gordon, *Synthesis*, Dec. 1984, pp. 1058–1061.

Chem Abst., vol. 121, No. 9, 28 Aug. 1994, Abstract No. 1080762.

*Primary Examiner*—C. Warren Ivy
*Assistant Examiner*—Raymond Covington
*Attorney, Agent, or Firm*—Charlotte L. Barney

[57] ABSTRACT

The present invention relates to heterocyclic benzenesulfonylimine derivatives and their use as inhibitors of Interleukin-1 (IL-1) action. Such inhibitors are useful in the treatment of various disease states as disclosed herein including rheumatoid arthritis, multiple sclerosis, diabetes mellitus, atherosclerosis, septic shock and pulmonary fibrosis.

12 Claims, No Drawings

HETEROCYCLIC BENZENESULFONYLIMINE DERIVATIVES AS INHIBITORS OF IL-1 ACTION

The present application has an effective international filing date of Nov. 3, 1994 as application PCT/US94/12575 which designated the U.S. and entered U.S. national phase under 35 USC 371 concurrently herewith, which application is a continuation of application Ser. No. 08/158,661 filed on Nov. 29, 1993, now abandoned.

The present invention relates to heterocyclic benzenesulfonylimine derivatives and their use as inhibitors of Interleukin-1 (IL-1) action. Such inhibitors are useful in the treatment of various disease states as disclosed herein including rheumatoid arthritis, multiple sclerosis, diabetes mellitus, atherosclerosis, septic shock and pulmonary fibrosis.

SUMMARY OF THE INVENTION

The present invention provides a method of inhibiting IL-1 action comprising administration of to a patient in need thereof an effective amount of a compound of the formula:

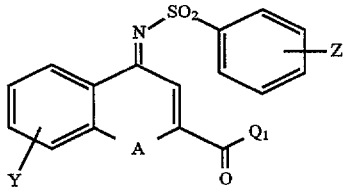

Formula I wherein
A is NH, O, or S;
$Q_1$ is —OR or —$NR_1R_2$; wherein R is hydrogen or $C_2$–$C_6$ alkyl radical of branched, straight chained, or cyclic configuration and $R_1$ and $R_2$ are each independently hydrogen or $C_1$–$C_6$ alkyl radical of branched, straight chained, or cyclic configuration;

Z is from 1 to 3 substituents chosen independently from the group: hydrogen, halogen, $C_1$–$C_4$ alkyl, and $C_1$–$C_4$ alkoxy;

Y is from 1 to 3 substituents chosen independently from the group: hydrogen, $C_1$–$C_4$ alkyl, $C_1$–$C_4$ alkoxy, and halogen.

Some of the compounds of the present invention are novel heterocyclic benzenesulfonylimine derivatives. These novel compounds are useful inhibitors IL-1 action. These novel compounds of Formula II are encompassed by the Formula I. The present invention provides novel heterocyclic benzenesulfonylimine derivatives of the formula:

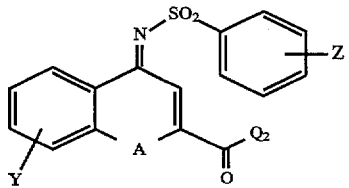

Formula II wherein
A is NH, O, or S;
$Q_2$ is —$OR_3$ or —$NR_1R_2$; wherein $R_3$ is $C_1$–$C_6$ alkyl radical of branched, straight chained, or cyclic configuration and $R_1$ and $R_2$ are each independently hydrogen or $C_1$–$C_6$ alkyl radical of branched, straight chained, or cyclic configuration with the provisos; 1) that when A is NH, $R_3$ is not $C_1$, 2) that when A is NH and Z is para-methyl, Y is not 7-methoxy, 6-methoxy, 5,8-dimethoxy, and 3) that when A is NH, Z is hydrogen, and $R_3$ is ethyl Y is not 5-ethyl-7-bromo;

Z is from 1 to 3 substituents chosen independently from the group: hydrogen, halogen, $C_1$–$C_4$ alkyl, and $C_1$–$C_4$ alkoxy;

Y is from 1 to 3 substituents chosen independently from the group: hydrogen, $C_1$–$C_4$ alkyl, $C_1$–$C_4$ alkoxy, and halogen.

The compounds encompassed by the provisos were disclosed as synthetic intermediates by Wright in *Syn*, 1058 (1984) and as NMDA antagonists in PCT Patent Application WO 92/15565 published Sep. 17, 1992. These compounds as disclosed herein, are active as inhibitors of IL-1 action. The compounds encompassed by the provisos are compounds of Formula I and should be considered within the scope of any method, use, or formulation claims.

DETAILED DESCRIPTION OF THE INVENTION

As used in this application:

a) the term "halogen" refers to a fluorine atom, chlorine atom, bromine atom, or iodine atom;

b) the terms "$C_1$–$C_4$ alkyl" refer to a branched or straight chained alkyl radical containing from 1 to 4 carbon atoms, such as methyl, ethyl, n-propyl, isopropyl, n-butyl, isobutyl, etc;

c) the term "$C_1$–$C_6$ alkyl" refer to a cyclic, branched, or straight chained alkyl radical containing from 1 to 6 carbon atoms, such as methyl, ethyl, n-propyl, isopropyl, n-butyl, isobutyl, n-pentyl, cyclopentyl, n-hexyl, cyclohexyl, etc;

d) the terms "$C_1$–$C_4$ alkoxy" refer to a straight or branched alkoxy group containing from 1 to 4 carbon atoms, such as methoxy, ethoxy, n-propoxy, isopropoxy, n-butoxy, isobutoxy, etc;

e) the term "pharmaceutically acceptable salts thereof" refers to either an acid addition salt or a basic addition salt;

The expression "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by Formula I or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline. Either the mono- or di-basic salts can be formed with those compounds.

As is readily apparent to those skilled in the art, the compounds of Formula I in which A is NH will exist as tautomers. Any reference to the compounds of Formula I or an intermediate thereof should be construed as referring to either tautomer. These tautomers may be depicted as:

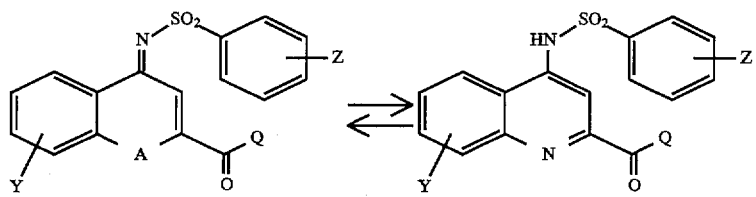

Examples of compounds encompassed by the present invention include:

- 5,7-Dichloro-4-[4-(fluoro)benzenesulfonylimino]-1,4-dihydroquinoline-2-carboxylic acid, methyl ester;
- 5,7-Dichloro-4-[4-(methoxy)benzenesulfonylimino]-1,4-dihydroquinoiline-2-carboxylic acid, methyl ester;
- 5,7-Dichloro-4-[benzenesulfonylimino]-1,4-dihydroquinoline-2-carboxylic acid, methyl ester;
- 5,7-Dichloro-4-[(4-methyl)benzenesulfonylimino]-1,4-dihydroquinoline-2-carboxylic acid, methyl ester;
- 5,7-Dichloro-4-[(4-chloro)benzenesulfonylimino]-1,4-dihydroquinoline-2-carboxylic acid, methyl ester;
- 5,7-Dichloro-4-[2-chlorobenzenesulfonylimino]-1,4-dihydroquinoline-2-carboxylic acid, methyl ester;
- 5,7-Dichloro-4-[3-chlorobenzenesulfonylimino]-1,4-dihydroquinoline-2-carboxylic acid, methyl ester;
- 5,7-Dichloro-4-[benzenesulfonylimino]-1,4-dihydroquinoline-2-carboxylic acid, ethyl ester;
- 5,7-Dichloro-4-[benzenesulfonylimino]-1,4-dihydroquinoline-2-carboxylic acid, propyl ester;
- 5,7-Dichloro-4-[benzenesulfonylimino]-1,4-dihydroquinoline-2-carboxylic acid, butyl ester;
- 5,7-Dichloro-4-[benzenesulfonylimino]-1,4-dihydroquinoline-2-carboxylic acid-N-methylamide;
- 5,7-Dichloro-4-[benzenesulfonylimino]-1,4-dihydroquinoline-2-carboxylic acid-N,N-dimethylamide;
- 5,7-Dichloro-4-[benzenesulfonylimino]]-4H-chromene-2-carboxylic acid, methyl ester;
- 4-[Benzenesulfonylimino]]-4H-thiochromene-2-carboxylic acid, methyl ester;
- 4-[Benzenesulfonylimino]]-4H-chromene-2-carboxylic acid, methyl ester.

A general synthetic procedure for preparing the compounds of Formula I in which A is NH is set forth in Scheme A. Since, the compounds of Formula II are encompassed by the Formula I the general synthetic procedure set out below also allows for the preparation of the compounds of Formula II in which A is NH. In Scheme A, all substituents, unless otherwise indicated, are as previously defined.

SCHEME A

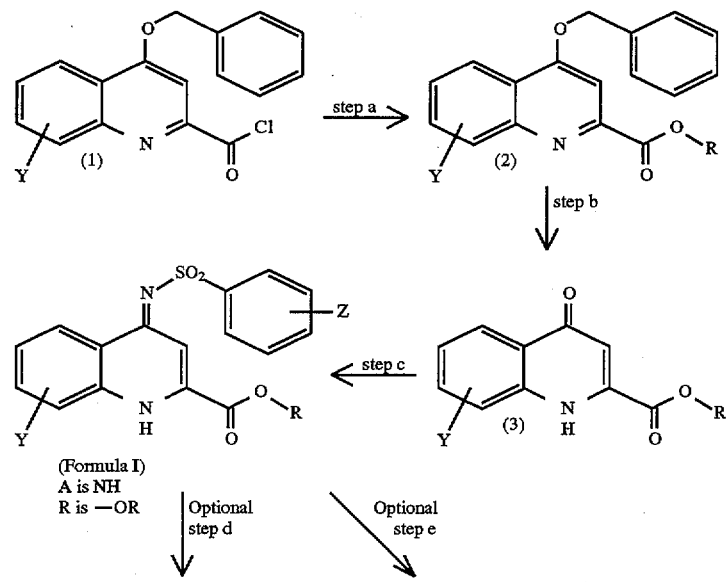

-continued
SCHEME A

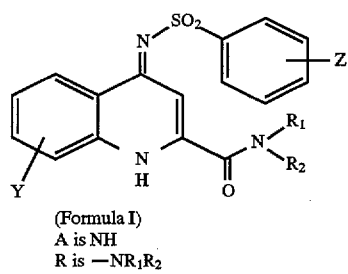

(Formula I)
A is NH
R is —NR₁R₂

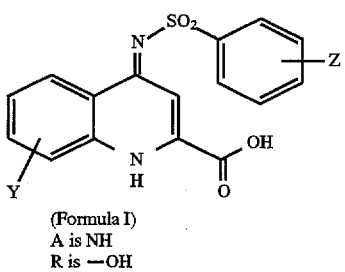

(Formula I)
A is NH
R is —OH

In general, in Scheme A, step a, an appropriate acid chloride of structure (1), known analogously in the art [P. Leeson, European Patent Application No. 0 303 387, published Feb. 15, 1989], is contacted with an appropriate alcohol to give an ester of structure (2).

An appropriate acid chloride of the structure (1) is one in which Y is as desired in the final product of the Formula I. An appropriate alcohol of the structure HOR is one which gives rise to compounds of Formula I in which $Q_1$ is —OR as desired in the final product of Formula I or gives rise to a $Q_1$ as desired in the final product of Formula I.

For example, an appropriate acid chloride of structure (1) is contacted with an appropriate alcohol. The reaction may be carried out in a suitable solvent, such as tetrahydrofuran, dimethylformamide, or the appropriate alcohol may be used as the solvent. The use of the appropriate alcohol as the solvent is preferred. The reaction is carried out in the presence of a suitable base, such as triethylamine, diisopropylethylamine, sodium carbonate, or sodium bicarbonate. The reaction requires from 1 to 8 hours. The product is isolated and purified by techniques well known in the art, such as evaporation in vacuo, extraction, chromatography with a suitable organic eluant, and recrystallization to give an ester of structure (2).

In Scheme A, step b, an ester of structure (2) is debenzylated to give a 1,4-dihydroquinol-4-one of structure (3).

For example, a compound of structure (2) is contacted with a suitable debenzylating agent, such as trifluoroacetic acid, at a temperature that is sufficient to remove the benzyl group but not degrade the starting material or product. The preferred temperature is 70° C. to 80° C. when the debenzylating agent is trifluoroacetic acid. The product is isolated and purified by techniques well known in the art, such as evaporation in vacuo, chromatography with a suitable organic eluant, and recrystallization to give a compound of structure (3).

In Scheme A, step c, a 1,4-dihydroquinol-4-one of structure (3) is contacted with an appropriate benzenesulfonyl isocyanate to a heterocyclic benzenesulfonylimine of Formula I in which A is NH.

An appropriate benzenesulfonyl isocyanate is one in which Z is as desired in the final product of the Formula I in which A is NH.

For example, a 1,4-dihydroquinol-4-one of structure (3) is contacted with an from 1 to 2 molar equivalents of an appropriate benzenesulfonyl isocyanate. The reaction is carried out in a suitable solvent, such as acetonitrile or propionitrile at temperatures of 20° C. to the refluxing temperature of the solvent. The product is isolated and purified by techniques well known in the art, such as evaporation in vacuo, chromatography with a suitable organic eluant, and recrystallization to give a compound of Formula I in which A is NH.

In Scheme A, optional step d, an appropriate compound of Formula I is contacted with an appropriate amine to give a compound of Formula I in which $Q_1$ is —NR₁R₂ and A is NH.

An appropriate compound of Formula I is one in which $Q_1$ is —OR, R is a $C_1$-$C_6$ alkyl, A is NH and Y and Z are as desired in the final product of the Formula I. An appropriate amine of the structure, HNR₁R₂ gives a compound of Formula I in which $Q_1$ is —NR₁R₂ as desired in the final product of Formula I in which A is NH.

For example, an appropriate compound of Formula I is contacted with an appropriate amine in a suitable solvent, such as methanol, ethanol, water, or dioxane. The reaction vessel may be sealed to prevent the escape of volatile amines from the reaction vessel. The reaction is carried out at temperatures from ambient temperature to the refluxing temperature of the solvent. The product is recovered by techniques well known in the art, such as extraction, evaporation in vacuo, chromatography with a suitable organic eluant, and recrystallization.

In Scheme A, optional step e, an appropriate compound of Formula I is hydrolyzed to give a compound of Formula I in which $Q_1$ is —OH and A is NH.

An appropriate compound of Formula I is one in which $Q_1$ is —OR, R is a $C_1$-$C_6$ alkyl, A is NH and Y and Z are as desired in the final product of the Formula I.

For example, an appropriate compound of Formula I is contacted with a suitable base, such as lithium hydroxide or sodium hydroxide. The reaction is carried out in a suitable solvent, such as water, tetrahydrofuran, methanol, water/tetrahydrofuran mixtures, and water/methanol mixtures. The reactants are typically stirred together for a period of time ranging from 2–24 hours and at a temperature range of from room temperature to reflux. The compound of Formula I in which $Q_1$ is —OH and A is NH is recovered from the reaction zone by acidification followed by filtration and may be purified by recrystallization as is known in the art.

The following examples present typical syntheses as described in Scheme A. These examples are understood to be illustrative only and are not intended to limit the scope of the invention in any way. As used in the following examples, the following terms have the meanings indicated: "g" refers to grams, "mg" refers to milligrams, "mmol" refers to millimoles, "mL" refers to milliliters, "°C" refers to degrees Celsius, "$R_f$" refers to retention "mp" refers to melting point, "dec" refers to decomposition, "TLC" refers to thin layer chromatography.

EXAMPLE 1

Scheme A, step a:
5,7-Dichloro-4-benzyloxyquinoline-2-carboxylic acid, ethyl ester Combine 5,7-dichloro-4-benzyloxyquinoline-2-acid chloride (1.83 g, 5 mmol), triethylamine (0.7 mL, 5.0 mmol), and ethanol (0.58 mL, 10 mmol) in tetrahydrofuran (25 mL). Stir at ambient temperature. After 18 hours evaporate in vacuo to give a residue. Chromatograph the residue on silica gel eluting with dichloromethane to obtain a solid. Recrystallize the solid from ethyl acetate/hexane to give the title compound as a solid: TLC $R_f$=0.33 (silica gel, dichloromethane); mp; 146°–147° C. Elem. Anal. calculated for $C_{19}H_{15}Cl_2NO_3$: C, 60.65; H, 4.02; N, 3.72. Found: C, 60.35; H, 4.17; N, 3.65.

EXAMPLE 2

Scheme A, step a:
5,7-Dichloro-4-benzyloxyquinoline-2-carboxylic acid, butyl ester Combine 5,7-dichloro-4-benzyloxyquinoline-2-acid chloride (1.83 g, 5 mmol), triethylamine (0.7 mL, 5.0 mmol), and butanol (1.04 mL, 10 mmol) in tetrahydrofuran (25 mL). Stir at ambient temperature. After 18 hours evaporate in vacuo to give a residue. Chromatograph the residue on silica gel eluting with dichloromethane to give a solid. Recrystallize the solid from ethyl acetate/hexane to give the title compound as a solid: TLC $R_f$=0.50 (silica gel, dichloromethane); mp; 130°–132° C. Elem. Anal. calculated for $C_{21}H_{19}Cl_2NO_3$: C, 62.39; H, 4.74; N, 3.46. Found: C, 62.20; H, 4.83; N, 3.22.

EXAMPLE 3

Scheme A, step b:
5,7-Dichloro-quinolin-4-one-2-carboxylic acid, ethyl ester

Combine 5,7-dichloro-4-benzyloxyquinoline-2-carboxylic acid, ethyl ester (1.14 g, 3.0 mmol) and trifluoroacetic acid (60 mL). Heat in an oil bath at 80° C. After 4 hours evaporate in vacuo. Add hexane and evaporate in vacuo to remove the residual trifluoroacetic acid and give a solid. Recrystallize the solid from acetonitrile to give the title compound as a solid: TLC $R_f$=0.33 (silica gel, 2% acetone/dichloromethane); mp;.256°–266° C. Elem. Anal. calculated for $C_{12}H_{19}Cl_2NO_3$: C, 50.37; H, 3.17; N, 4.90. Found: C, 50.39; H, 3.31; N, 4.92.

EXAMPLE 4

Scheme A, step b:
5,7-Dichloro-quinolin-4-one-2-carboxylic acid, butyl ester

Combine 5,7-dichloro-4-benzyloxyquinoline-2-carboxylic acid, butyl ester (1.35 g, 3.3 mmol) and trifluoroacetic acid (65 mL). Heat in an oil bath at 75° C. After 3 hours evaporate in vacuo. Add dichloromethane and evaporate in vacuo to remove the residual trifluoroacetic acid to give a residue. Recrystallize the residue from acetonitrile to give the title compound as a solid: mp; 191°–193° C.

EXAMPLE 5

Scheme A, step c:
5,7-Dichloro-4-[benzenesulfonylimino]-1,4-dihydroquinoline-2-carboxylic acid, ethyl ester Combine 5,7-dichloro-quinolin-4-one-2-carboxylic acid, ethyl ester (0.59 g, 2.1 mmol) and benzenesulfonyl isocyanate (0.56 mL, 4.2 mmol) in acetonitrile (10 mL). Heat to reflux under an inert atmosphere. After 16 hours, quench with methanol (5 mL). Evaporate in vacuo. Chromatograph on silica gel eluting with 2% acetone/dichloromethane. Recrystallize from acetonitrile to give the title compound as a solid: TLC $R_f$=0.31 (silica gel, 2% acetone/dichloromethane); mp; 184°–185° C. Elem. Anal. calculated for $C_{18}H_{14}Cl_2N_2O_4S$: C, 50.83; H, 3.32; N, 6.59. Found: C, 51.04; H, 3.33; N, 6.56.

EXAMPLE 6

Scheme A, step c:
5,7-Dichloro-4-[benzenesulfonylimino]-1,4-dihydroquinoline-2-carboxylic acid, butyl ester Combine 5,7-dichloro-quinolin-4-one-2-carboxylic acid, butyl ester (1.00 g, 3.2 mmol) and benzenesulfonyl isocyanate (0.85 mL, 6.3 mmol) in acetonitrile (15 mL). Heat to reflux under an inert atmosphere. After 16 hours, quench with methanol (5 mL). Evaporate in vacuo. Chromatograph on silica gel eluting with 2% acetone/dichloromethane. Recrystallize from ethyl acetate/hexane to give the title compound as a solid: TLC $R_f$=0.38 (silica gel, 2% acetone/dichloromethane); mp; 94°–95° C. Elem. Anal. calculated for $C_{20}H_{18}Cl_2N_2O_4S$: C, 52.98; H, 4.00; N, 6.18. Found: C, 53.27; H, 3.95; N, 6.12.

EXAMPLE 7

Scheme A, optional step d:
5,7-Dichloro-4-[benzenesulfonylimino]-1,4-dihydroquinoline-2-carboxylic acid-N-methylamide Combine 5,7-dichloro-4-[benzenesulfonylimino]-1,4-dihydroquinoline-2-carboxylic acid, methyl ester (1.0 g, 2.4 mmol) and 40% methylamine in water (25 mL) and dioxane (50 mL). Stopper and stir for 18 hours. Evaporate in vacuo to give a yellow oil. Dissolve the oil in water (15 mL) and add 1M hydrochloric acid solution (15 mL). Stir for 15 minutes and then filter to obtain a solid. Rinse the solid with 1M hydrochloric acid solution and water. Recrystallize from acetonitrile/water to give the title compound as a solid: mp; 196°–197° C. Elem. Anal. calculated for $C_{17}H_{13}Cl_2N_3O_3S \cdot H_2O$: C, 47.68; H, 3.53; N, 9.81. Found: C, 47.55; H, 3.42; N, 9.78.

A general synthetic procedure for preparing these compounds of Formula I in which A is O or S is set forth in Scheme B. Since, the compounds of Formula II are encompassed by the Formula I the general synthetic procedure set out below also allows for the preparation of the compounds of Formula II in which A is O or S. In Scheme B, all substituents, unless otherwise indicated, are as previously defined.

SCHEME B

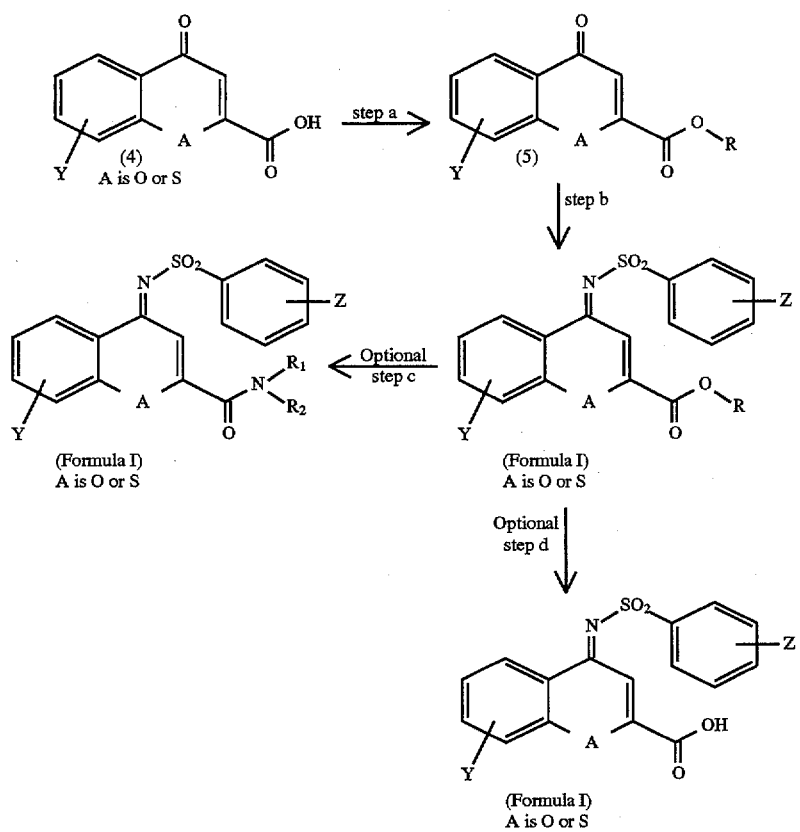

In Scheme B step a, an appropriate acid of structure (4) in which A is O or S, known analogously in the art, [Chromenes, Chromanones, and Chromones, edited by G. P. Ellis (John Wiley & Sons 1977)] is contacted with an appropriate alcohol to give an ester of structure (5).

An appropriate acid of structure (4) is one in which A is O or S and Y is as desired in the final product of the Formula I. An appropriate alcohol of the structure HOR is one which gives rise to compounds of Formula I in which $Q_1$ is —OR as desired in the final product of Formula I or gives rise to a $Q_1$ as desired in the final product of Formula I.

For example, an acid of structure (4) is contacted with an appropriate alcohol in the presence of an acid, such as sulfuric acid. The appropriate alcohol is used as the solvent. The reaction is carried out at temperatures from ambient temperature to the refluxing temperature of the alcohol. The product is recovered by techniques well known in the art, such as extraction, evaporation in vacuo, chromatography with a suitable organic eluant, and recrystallization to give an ester of structure (5).

In Scheme B, step b, a compound of structure (5) is contacted with an appropriate benzenesulfonyl isocyanate to give a heterocyclic benzenesulfonylimine of Formula I in which A is O or S.

An appropriate benzenesulfonyl isocyanate is one is which Z is as desired in the final product of the Formula I in which A is O or S.

For example, a compound of structure (5) is contacted with an appropriate benzenesulfonyl isocyanate. The reaction is carried out in a suitable solvent, such as acetonitrile or propionitrile at temperatures from ambient temperature to the refluxing temperature of the solvent. The product is recovered by techniques well known in the art, such as evaporation in vacuo, chromatography with a suitable organic eluant, and recrystallization to give a compound of Formula I in which A is O or S.

In Scheme B, Optional step c, an appropriate compound of Formula I is contacted with an appropriate amine to give a compound of Formula I in which $Q_1$ is —$NR_1R_2$ and A is O or S.

An appropriate compound of Formula I is one in which $Q_1$ is —OR, R is a $C_1$-$C_6$ alkyl, A is O or S, and Y and Z are as desired in the final product of the Formula I. An appropriate amine of the structure, $HNR_1R_2$ gives a compound of Formula I in which $Q_1$ is —$NR_1R_2$ as desired in the final product of Formula I in which A is O or S.

For example, an appropriate compound of Formula I is contacted with an appropriate amine in a suitable solvent, such as methanol, ethanol, water, or dioxane. The reaction vessel may be sealed to prevent the escape of volatile amines from the reaction vessel. The reaction is carried out at temperatures from ambient temperature to the refluxing temperature of the solvent. The product is recovered by techniques well known in the art, such as extraction, evaporation in vacuo, chromatography with a suitable organic eluant, and recrystallization.

In Scheme B, Optional step d, an appropriate compound of Formula I is hydrolyzed to give a compound of Formula I in which $Q_1$ is —OH and A is O or S.

An appropriate compound of Formula I is one in which $Q_1$ is —OR, R is a $C_1$-$C_6$ alkyl, A is O or S, and Y and Z are as desired in the final product of the Formula I.

For example, an appropriate compound of Formula I is contacted with a suitable base, such as lithium hydroxide or sodium hydroxide. The reactants are typically stirred together for a period of time ranging from 2-24 hours and at a temperature range of from room temperature to reflux. The acid of Formula I in which A is O or S is recovered from the reaction zone by acidification followed by filtration and may be purified by recrystallization as is known in the art.

The following examples present typical syntheses as described in Scheme B. These examples are understood to be illustrative only and are not intended to limit the scope of the invention in any way. As used in the following examples, the following terms have the meanings indicated: "g" refers to grams, "mmol" refers to millimoles, "mL" refers to milliliters, "°C" refers to degrees Celsius, "mp" refers to melting point.

EXAMPLE 8

Scheme B, step a:
Chromone-2-carboxylic acid methyl ester

Combine chromone-2-carboxylic acid (2.0 g, 10.5 mmol) and methanol (25 mL). Add sulfuric acid (2.5 mL) and heat to reflux. After 2 hours pour the reaction mixture into ice water and filter. Rinse the filter cake with water and a cold dilute aqueous solution of sodium bicarbonate. Chromatograph on silica gel eluting with tetrahydrofuran to give a residue. Recrystallize the residue from methanol to give the title compound as a solid: mp; 120°–122° C.

EXAMPLE 9

Scheme A, step b:
4-[Benzenesulfonylimino]-4H-chromene-2-carboxylic acid, methyl ester Combine chromone-2-carboxylic acid methyl ester (0.341 g, 1.66 mmol) and benzenesulfonyl isocyanate (0.365 g, 1.88 mmol) in acetonitrile (5.0 mL) and reflux. After 24 hours, quench the reaction with methanol (1 mL). Concentrate in vacuo and triturate with hexane. Filter to obtain a paste. Recrystallize the paste from methanol to obtain a solid. Recrystallize from methanol to give the title compound as a solid: mp; 144°–146° C.

Interleukin-1 (IL-1) consists of two polypeptides, termed IL-1α and IL-1β, that belong to a family of cytokines that also includes tumor necrosis factor (TNFα) and IL-6. These cytokines have overlapping biological properties, including the ability to stimulate T and B lymphocytes and to effect the expression of proteins involved in many immunological and inflammatory responses.

Agents which inhibit IL-1 action may do so by several mechanisms including: inhibition of IL-1 production by inhibition of the expression, synthesis, or release of IL-1; antagonism at an IL-1 receptor; inhibition of the IL-1 induced amplification of IL-1 production; or inhibition of IL-1 induced production of other cytokines; etc.

It is known, for example, that IL-1 is produced by epithelial cells and stimulates fibroblast proliferation and release of proteolytic enzymes (e.g. collagenase) and prostaglandins in inflammatory processes, i.e. rheumatoid arthritis. See Durom, S. K.; Schmidt, J. A.; Oppenheim, J. J.; *Interleukin 1:an Immunological Perspective, Ann. Rev. Immunol.* 3, 263–287 (1985), Otterness, I. G.; Bliven, M. L.; Downs, J. T.; Natoli, E. J.; Hanson, D. C.; *Inhibition of Interleukin-1 Synthesis by Tenidap: a New Drug for Arthritis, Cytokine,* 3, 277–283 (1991), and Miyasaka, N.; Sato, K.; Goto, M.; Sasano, M.; Natsuyma, M.; Inoue, K.; and Nishioks, K., *Augmented Interleukin-1 Production and HLA-DR Expression in the Synovium of Rheumatoid Arthritis Patients, Arthritis and Rheumatism,* 31, 480–486 (1988). Thus agents which inhibit IL-1 action would be useful in the treatment of rheumatoid arthritis.

It has also been shown that IL-1 may affect the pathogenesis of atherosclerosis directly, by stimulating smooth muscle cell proliferation or, indirectly, through the action of platelet-derived growth factor (PDGF). See Jackson, R. L. and Ku, G., *Interleukin-1β, its Role in the Pathogenesis of Atherosclerosis and Agents that Inhibit its Action, Current Drugs: Anti-atherosclerotic Agents,* pp B31–B42 (October 1991). In addition, Tenidap, an agent known to block IL-1 production, reduces the total level of serum cholesterol, serum LDL cholesterol and serum triglycerides in a mammal having an arthritic condition for which Tenidap is being administered. See U.S. Pat. No. 5,122,534 (Feb. 8, 1991). Thus agents which inhibit IL-1 action may also be useful in the prophylactic treatment of atherosclerosis.

In addition, it has also been postulated that macrophages infiltrating the pancreatic islets may play a role in the destruction of β-cells and that cytokines, in particular IL-1, released locally from the macrophages may be the toxic molecules causing β-cell destruction in insulin-dependent diabetes mellitus (IDDM). See Sandler, S., Eizirik, D., Svensson, C., Strandell, E., Welsh, M. and Welsh, N., *Biochemical and Molecular Action of Interleukin 1 on Pancreatic β-Cells, Autoimmunity,* 10, 241–253 (1991). Thus agents which inhibit IL-1 action may also be useful in the treatment of diabetes mellitus.

A correlation has also been shown between increased IL-1 production and the clinical course of multiple sclerosis (MS). It has been demonstrated that there is a significant increase in IL-1α production by cultured blood mononuclear cells for patients with MS, with patients in the active phase of relapsing MS showing the greatest increase in IL-1α production. See Matsuda, M., Tsukada, N., Miyagi, K., and Yanagisawa, N., *Increased Interleukin-1 production by peripheral blood mononuclear cells in patients with multiple sclerosis, Journal of the Neurological Sciences,* 102, 100–104 (1991). Thus agents which inhibit IL-1 action may also be useful in the treatment of multiple sclerosis.

Studies have also shown that IL-1 receptor antagonists might be useful for the treatment of incipient or established pulmonary fibrosis. See Piguet, P., Vesin, C., Grau, G., Thompson, R., *Interleukin-1 Receptor Antagonist (IL-1ra) Prevents or Cures Pulmonary Fibrosis Elicited in Mice By Bleomycin or Silica, Cytokine,* 5, 57–61 (1993). Thus agents which inhibit IL-1 action may also be useful in the treatment of pulmonary fibrosis.

It has also been suggested that IL-1 receptor antagonists may play a role in reducing mortality from septic shock. See Ohlsson, K., Bjork, P., Bergenfeldt, M., Hageman, R., and Thompson, R., *Interleukin-1 Receptor Antagonist Reduces Mortality from Endotoxin Shock, Nature,* 348, 550–552 (1990). Thus agents which inhibit IL-1 action may also be useful in the treatment of septic shock.

The compounds of Formula I inhibit IL-1 action. One mechanism for inhibiting IL-1 action is to inhibit IL-1 production. Inhibition of IL-1 production was tested using lipopolysaccharide (LPS) stimulated macrophages. Inhibition of IL-1 induced production of cytokines was tested by measuring the inhibition of TNFα (tumor necrosis factor alpha) synthesis from IL-1 stimulated macrophages. The protocols for these test procedures are described below.

Endotoxin-Induced Interleukin-1 Beta Release by Human Macrophages

Objective

The objective of this test is to determine the inhibitory concentrations for the test compounds against endotoxin-induced interleukin-1 beta (IL-1β) release (production) by human peripheral blood monocyte-derived macrophages.

Source

The source of the human peripheral blood monocyte-derived macrophages is as follows: Venous blood is collected from healthy volunteers in 10 mM sodium citrate (2 mL sterile sodium citrate for 40 mL blood). Mononuclear cells are isolated with the Leucoprep tubes (Becton Dickenson, product number 2752 or 2751) spun at 1500 g for 15 minutes. Aliquots of $3 \times 10^6$ mononuclear cells are added to 24-well tissue culture plates (Corning) in RPMI-1640. After one hour incubation at 37° C., non-adherent cells are gently rinsed off. The adherent cells (macrophages) are given back fresh medium RPMI-1640, 1 mL/well.

Procedure

Macrophage monolayer cultures are pretreated with compounds one hour prior to endotoxin (20 ng/mL, *Salmonella typhimurium*, Re-mutant, from Ribi Immuchem.) stimulation. Compounds dissolved in 95% ethanol or DMSO would require additional monolayer cultures treated with 10 or 2.5 μl 95% ethanol or DMSO, respectively. Culture supernatants are collected 24 hours later and are tested for IL-1β using a commercial ELISA kit (Cistron).

Analysis of Results

The IL-1β concentration in the culture supernatant is calculated by a standard curve generated from a series of known concentrations. Potency of compound is reported in $IC_{50}$ (μM).

Results:

| Compound | $IC_{50}$ |
|---|---|
| 5,7-Dichloro-4-[benzenesulfonylimino]-1,4-dihydroquinoline-2-carboxylic acid, methyl ester | 6 μM |
| 5,7-Dichloro-4-[benzenesulfonylimino]-1,4-dihydroquinoline-2-carboxylic acid, ethyl ester | 2 μM |
| 5,7-Dichloro-4-[benzenesulfonylimino]-1,4-dihydroquinoline-2-carboxylic acid, butyl ester | 3 μM |
| 5,7-Dichloro-4-[benzenesulfonylimino]-1,4-dihydroquinoline-2-carboxylic acid-N-methylamide | 3 μM |
| 4-[Benzenesulfonylimino]-4H-chromene-2-carboxylic acid, methyl ester | 3 μM |

Interleukin-1-Beta-Induced Tumor Necrosis Factor Alpha Release by Human Macrophages Objective To determine the inhibitory concentrations for the test compounds against interleukin-1 beta (IL-1β)-induced tumor necrosis factor alpha (TNFα) release by human peripheral blood monocyte-derived macrophages. It should be understood that this is a test of the ability of the test compounds to modulate, i.e. inhibit, the activity of IL-1β by measuring the inhibition of IL-1β induced release of TNFα.

Source Human peripheral blood monocyte-derived macrophages:

Venous blood is collected form healthy volunteers in 10 mM sodium citrate (2 mL sterile sodium citrate for 40 mL blood). Mononuclear cells are isolated with the Leucoprep tubes (Becton Dickinson, product number 2752 or 2751) spun at 1500 g for fifteen minutes. Aliquots of $3 \times 10^6$ mononuclear cells are added to 24-well tissue culture plates (Corning) in RPMI-1640. After 1 hour incubation at 37° C., non-adherent cells are gently rinsed off. The adherent cells (macrophages) are given back fresh medium RPMI-1640, 1 mL/well.

Procedure

Macrophage monolayer cultures are pretreated with compounds one hour prior to IL-1β (20 ng/mL, recombinant human IL-1β) stimulation. Compounds dissolved in 95% ethanol or DMSO would require additional monolayer cultures treated with 10 or 2.5 μl 95% ethanol or DMSO, respectively. Culture supernatants are collected 24 hours later and are tested for TNF-α using a commercial ELISA kit (Cistron).

Analysis of Results

The TNF-α concentration in the culture supernatant is calculated by a standard curve generated from a series of known concentrations. Potency of compound is reported in $IC_{50}$ (μM).

Results:

| Compound | $IC_{50}$ |
|---|---|
| 5,7-Dichloro-4-[benzenesulfonylimino]-1,4-dihydroquinoline-2-carboxylic acid, methyl ester | 3 μM |
| 5,7-Dichloro-4-[benzenesulfonylimino]-1,4-dihydroquinoline-2-carboxylic acid, ethyl ester | 3 μM |
| 5,7-Dichloro-4-[benzenesulfonylimino]-1,4-dihydroquinoline-2-carboxylic acid, butyl ester | 5 μM |
| 5,7-dichloro-4-[benzenesulfonylimino]-1,4-dihydroquinoline-2-carboxylic acid-N-methylamide | 4 μM |
| 4-[Benzenesulfonylimino]-4H-chromene-2-carboxylic acid, methyl ester | 2 μM |

The compounds of the present invention may be administered by a variety of routes. They are effective if administered orally. The compounds may also be administered parenterally (i.e. subcutaneously, intravenously, intramuscularly, intraperitoneally, or intrathecally).

In order to exhibit these therapeutic properties, the compounds need to be administered in a quantity sufficient to inhibit IL-1 action. The dosage range at which these compounds exhibit this inhibitory effect can vary widely depending upon the particular disease being treated, the severity of the patient's disease, the patient, the particular compound being administered, the route of administration, and the presence of other underlying disease states within the patient, etc. Typically the compounds exhibit their therapeutic effect at a dosage range of from about 0.1 mg/kg/day to about 50 mg/kg/day for any of the diseases or conditions listed above.

Pharmaceutical compositions can be manufactured utilizing techniques known in the art. Typically an effective amount of the compound will be admixed with a pharmaceutically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of Formula I can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art.

As used in this application:
a) the "patient" refers to warm blooded animals such as, for example guinea pigs, mice, rats, cats, rabbits, dogs, monkeys, chimpanzees, and human;
b) the term "treat" refers to the ability of the compounds to either relieve, alleviate, or slow the progression of the patient's disease.
c) the term "an effective amount" refers to an amount which is effective, upon single or multiple dose administration to the patient, in inhibiting IL-1 action.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951; 3,797,494; 3,996,934; and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is nonporous. The pharmaceutically effective compound dissolves in and diffuses through the matrix itself. Release by microporous flow occurs when the pharmaceutically effective compound is transported through a liquid phase in the pores of the matrix.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art.

What is claimed is:

1. The method of inhibiting IL-1 action in a patient in need thereof by administering to the patient a therapeutically effective amount of compounds of the structure

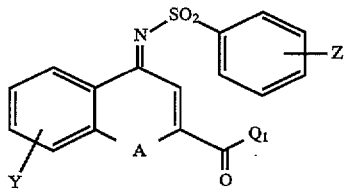

Formula I wherein A is NH, O, or S;

$Q_1$ is —OR or —$NR_1R_2$; wherein R, $R_1$ and $R_2$ are each independently hydrogen or $C_1$–$C_6$ alkyl radical of branched, straight chained, or cyclic configuration, wherein in the case of a cyclic configuration is $C_3$–$C_6$ cycloalkyl;

Z is from 1 to 3 substituents chosen independently from the group: halogen, $C_1$–$C_4$ alkyl, and $C_1$–$C_4$ alkoxy;

Y is from 1 to 3 substituents chosen independently from the group: $C_1$–$C_4$ alkyl, $C_1$–$C_4$ alkoxy, and halogen.

2. The method according to claim 1 for the treatment of an inflammatory disease.

3. The method according to claim 1 for the treatment of multiple sclerosis.

4. The method according to claim 1 for the treatment of insulin-dependent diabetes mellitus.

5. The method according to claim 1 for the treatment or prevention of atherosclerosis.

6. The method according to claim 1 for the treatment or prevention of septic shock.

7. The method according to claim 1 for the treatment of pulmonary fibrosis.

8. A method according to claim 1 for the treatment of rheumatoid arthritis.

9. A compound of formula

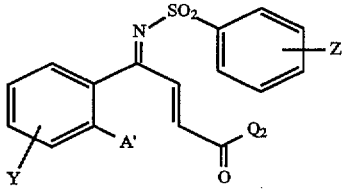

Formula II wherein A' is O or S;

$Q_2$ is —$OR_3$ or —$NR_1R_2$; wherein $R_1$, $R_2$ and $R_3$ are each independently $C_1$–$C_6$ alkyl radical of branched, straight chained, or cyclic configuration, wherein in the case of a cyclic configuration is $C_3$–$C_6$ cycloalkyl;

Z is from 1 to 3 substituents chosen independently from the group: halogen, $C_1$–$C_4$ alkyl, and $C_1$–$C_4$ alkoxy;

Y is from 1 to 3 substituents chosen independently from the group: $C_1$–$C_4$ alkyl, $C_1$–$C_4$ alkoxy, and halogen.

10. The compound according to claim 9 which is 4-[benzenesulfonylimino]]-4H-chromene-2-carboxylic acid, methyl ester.

11. The compound according to claim 9 which is 4-[benzenesulfonylimino]]-4H-thiochromene-2-carboxylic acid, methyl ester.

12. A pharmaceutical composition comprising an effective amount of a compound according to claim 1 in admixture with a pharmaceutically acceptable carrier.

* * * * *

UNITED STATES PATENT AND TRADEMARK OFFICE
CERTIFICATE OF CORRECTION

PATENT NO. : 5,668,143
DATED : September 16, 1997
INVENTOR(S) : Ku, et. al.

It is certified that error appears in the above-identified patent and that said Letters Patent is hereby corrected as shown below:

Column 1, line 34, reads--"$C_{2-}$" and should read --$C_{1-}$--.

Signed and Sealed this

Thirtieth Day of June, 1998

Attest:

BRUCE LEHMAN

*Attesting Officer*     *Commissioner of Patents and Trademarks*